United States Patent [19]
Vetter et al.

[11] Patent Number: 5,803,918
[45] Date of Patent: Sep. 8, 1998

[54] SYRINGE FOR MEDICINAL PURPOSES

[75] Inventors: Helmut Vetter, Ravensburg; Thomas Otto, Vogt; Eugen Frasch, Oberteuringen, all of Germany; Ralf Bitdinger, Herbeys, France

[73] Assignee: Becton Dickinson and Company, Franklin Lakes, N.J.

[21] Appl. No.: 831,840

[22] Filed: Apr. 2, 1997

Related U.S. Application Data

[63] Continuation of Ser. No. 674,047, Jul. 1, 1996, abandoned, and a continuation of Ser. No. 356,357, filed as PCT/EP94/01401 May 3, 1994, abandoned.

[30] Foreign Application Priority Data

| May 6, 1993 | [DE] | Germany | 43 14 987.1 |
| Sep. 14, 1993 | [DE] | Germany | 43 31 137.7 |

[51] Int. Cl.⁶ ..................................................... A61M 5/00
[52] U.S. Cl. ........................................... 604/110; 604/220
[58] Field of Search ..................................... 604/110, 187, 604/208, 218–222, 228

[56] References Cited

U.S. PATENT DOCUMENTS

| 772,114 | 10/1904 | Pappenheim | 604/220 |
| 3,747,812 | 7/1973 | Karman et al. | 222/387 |
| 4,267,846 | 5/1981 | Kontos | 604/220 |
| 4,386,606 | 6/1983 | Tretinyak et al. | 604/220 |
| 4,391,273 | 7/1983 | Chiquliar-Arias | 604/110 |
| 4,704,105 | 11/1987 | Adorjan et al. | 604/222 |
| 4,711,637 | 12/1987 | Leigh et al. | 604/220 |
| 4,883,471 | 11/1989 | Braginetz et al. | 604/195 |
| 4,946,441 | 8/1990 | Laderoute | 604/110 |
| 5,205,824 | 4/1993 | Mazur | 604/110 |
| 5,222,945 | 6/1993 | Basnight | 604/110 |

FOREIGN PATENT DOCUMENTS

| 0 242 956 A1 | of 0000 | European Pat. Off. . |
| 0 409 134A1 | 7/1990 | European Pat. Off. . |
| 447245 | 7/1927 | Germany . |
| 29 45 869A1 | 5/1981 | Germany . |
| WO 95/35128 | of 0000 | WIPO . |

*Primary Examiner*—John D. Yasko
*Attorney, Agent, or Firm*—Allen W. Wark

[57] ABSTRACT

The syringe for medicinal purposes features a syringe barrel (1), one end of which is formed as an adapter (2) for a cannula or a closure (3), e.g., in the form of a tip cap, and of a plunger (4), arranged within the syringe barrel (1), and movable by a piston rod (5). At the end of the syringe barrel (1) facing away from the adapter (2), a plunger brake (6) is arranged, which is formed by a rest piece surrounding the syringe barrel (1) and connected removably to it. The rest piece has a projection extending into the lumen of the syringe barrel (1), which forms a stop for the side of the plunger (4) away from the adapter (2).

14 Claims, 4 Drawing Sheets

FIG.4a
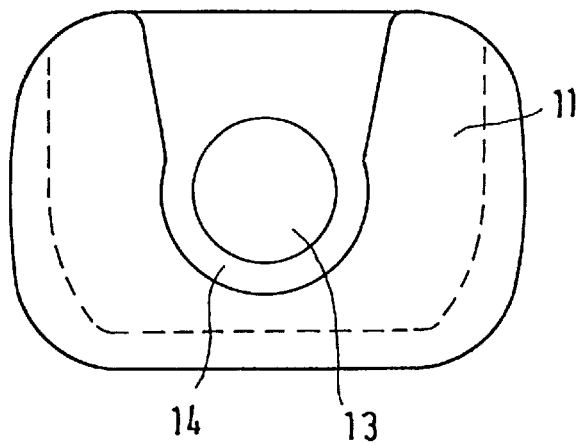
FIG.4c
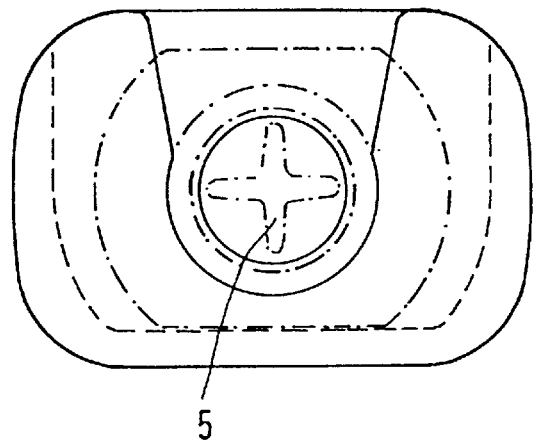
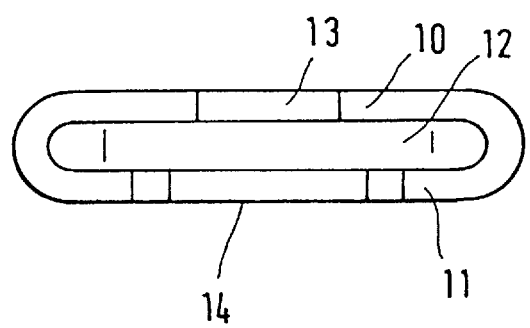
FIG.4b
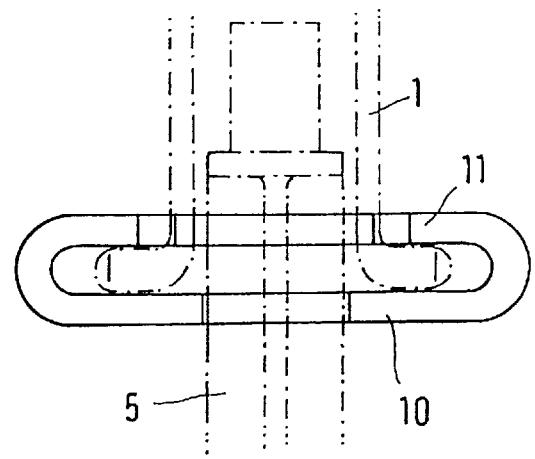
FIG.4d

SYRINGE FOR MEDICINAL PURPOSES

This application is a continuation of application Ser. No. 08/356,357, filed Dec. 20, 1994 now abandoned and a continuation of Ser. No. 08/674,047 filed Jul. 1, 1996 now abandoned. This is a request for filing a continuation application under 37 CFR §1.62 of prior application Ser. No. 08/356,357, filed on Dec. 20, 1994 entitled SYRINGE FOR MEDICINAL PURPOSES which is a 371 of PCT/EP94/01401 filed May 3, 1994.

FIELD OF THE INVENTION

The invention pertains to a syringe for medicinal purposes, with a syringe barrel, one end of which is designed as an adapter for a cannula or a closure piece, e.g., in the form of a tip cap, and with a plunger arranged in the syringe barrel and movable via a piston rod.

BACKGROUND

Syringes of this type are increasingly being marketed, especially as ready-to-use syringes in prefilled form, for self-administration by the patient, as has long been the case, especially for regular administration of insulin in diabetics.

In the case of unskilled or infirm people, there is a risk that before application the plunger will accidentally be pulled out of the syringe barrel so that, as a rule, the product is no longer usable.

The invention has as its object the design of a syringe of the initially mentioned type in such a way that the plunger cannot get out of the barrel, or, if so, only with difficulty.

SUMMARY OF THE INVENTION

This goal is achieved in accordance with the invention in that on the end of the syringe barrel, away from the adapter, a plunger brake is arranged, which is formed by a rest piece surrounding the syringe barrel and attached removably to it, which has a projection extending into the lumen of the barrel, which forms a stop for the side of the plunger away from the adapter.

The advantage achieved with the invention lies, first of all, in the fact that the projection extending into the lumen of the syringe barrel exerts a braking effect on the plunger, so that even in the case of incorrect manipulation of the syringe by the patient during use, so long as excessive force is not applied, the plunger cannot come out of the syringe barrel.

Additional advantages arise in the course of manufacturing, since during the post-sterilization of solutions prefilled into the syringe barrel, the plunger is frequently forced out of the barrel by the pressure differences that arise. The use of the plunger brake prevents the plunger from being forced out of the barrel, for example, by an air bubble present in the barrel. In this process, the plunger brake can be sterilized along with the unit, if, for example, this is made of polypropylene. As a result, the pharmaceutical safety of the syringe as a whole is increased. Since the plunger brake is placed removably on the syringe barrel, it can be removed from the syringe after use; disposal is simplified by separation of the different materials.

In a first, advantageous embodiment of the invention, the rest piece is designed as an annular piece, and the projection is designed as fingers extending axially into the barrel, wherein the freely projecting end of the finger forms the stop for the plunger.

In a preferred embodiment of the invention, the annular piece has a separation slit on the side opposite the finger. In this way, the annular piece can especially easily be clipped onto the barrel from the side.

Advantageously, the annular piece is sleeve-shaped, so that it does not interfere with handling of the syringe.

For easier handling, the annular piece can be provided on its outer surface with a riffling travelling in the circumferential direction. This provides additional security when holding or handling the syringe. For this purpose, it can also be provided that the annular piece has two radially extending, diametrically opposite wings that form a finger rest. This is especially advantageous when syringes with very small volumes are used.

To achieve the best possible retention, the finger can advantageously lie against the inner wall of the syringe barrel. In this way it is also ensured that the finger will not interfere with actuation of the piston rod.

In order to also be able to screw the piston rod without difficulty into the plunger, the invention also provides that the piston rod is tapered in the area adjacent to the piston rod thread provided for connection to the plunger.

In a second advantageous embodiment of the invention, which is provided for syringes in which the end of the syringe barrel away from the adapter has an annular projection extending radially outward, the rest piece is formed by a flat slip-on piece consisting of two disks separated by an interval, wherein the two disks are connected at the edges and between them, form a receiving pocket for the annular projection of the syringe cylinder, open toward one edge, and wherein the disk away from the adapter is provided with a circular opening coaxial to the syringe barrel, the diameter of which is smaller than the internal diameter of the barrel, and the other disk has a recess, open toward the edge, for passage of the barrel.

In this embodiment, the edge of the coaxial opening in the one disk forms the stopper for the plunger. This slide-on piece guarantees firm connection with the cylinder and can also be designed such that it simultaneously forms a finger rest. Since the piston rod extends through the opening into one disk, unintentional removal of the plunger brake is not possible, at least with the piston rod mounted in place.

The recess advantageously has an edge shaped like the arc of a circle, coaxial with the circular opening, which surrounds the syringe barrel by somewhat more than 180 degrees and expands toward the edge of the disk. In this way, the slip-on piece can be connected simply and nevertheless firmly to the syringe barrel.

To prevent the piston rod, once placed in the syringe barrel, from being able to be accidentally withdrawn, it is also provided that the wall of the circular opening is designed as a cone mantle surface tapering toward the needle adapter, and the piston rod has on its end facing the plunger a radially outwardly projecting annular flange, the outer mantle surface of which likewise tapers conically toward the stopper, wherein the opening and/or the annular flange is designed to be elastic, at least in its marginal area.

It was found to be especially advantageous if the annular flange is received in a form-fitting way by the circular opening.

BRIEF DESCRIPTION OF THE DRAWINGS

In the following, the invention will be explained in greater detail, based on exemplified embodiments shown in the drawings, which show.

DETAILED DESCRIPTION OF THE PREFERRED EMBODIMENTS

Figure 1:
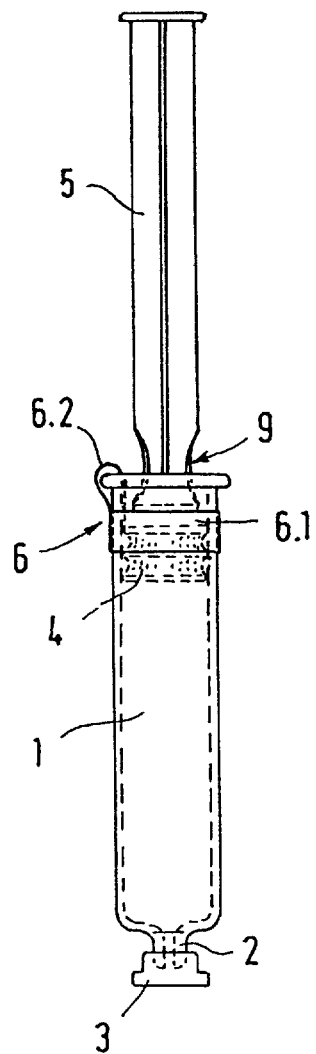
FIG. 1 a syringe in accordance with the invention in a first embodiment, in side view, with the plunger brake clipped on, FIG. 2 a perspective view of the plunger brake in accordance with FIG. 1, FIG. 3 an additional embodiment of the plunger brake with syringe cylinder only partially represented, in partial figure a before and in partial figure b after placement, in each case in perspective view, FIG. 4 in partial figures a to d a plunger brake in cross section or top view, in each case shown with and without the syringe barrel, FIG. 5 an additional embodiment similar to FIG. 3, prior to insertion of the piston rod, and FIG. 6 the object in accordance with FIG. 5, but after insertion of the piston rod.

The syringe for medicinal purposes shown in the drawing consists of a syringe barrel 1, one end of which is designed as an adapter 2 for a cannula or—as shown in FIG. 1—for a closure piece 3 in the form of a tip cap. In the syringe barrel 1, a plunger 4 is arranged, which can be moved with the aid of a piston rod 5.

At the end of the syringe barrel 1 away from the cannula adapter 2, a plunger brake 6 is arranged. The plunger brake 6 consists, in detail, in a first embodiment shown in FIGS. 1 and 2, of a first annular piece 6.1, surrounding the barrel 1, and a finger 6.2 projecting into the interior of the barrel 1, connected to the annular piece 6.1. Here the free end of the finger 6.2 forms a stop for the plunger 4.

The plunger brake 6 prevents the plunger 4 from being accidentally pulled out of the barrel 1 in the case of incorrect use of the syringe, for example by a unskilled patient.

Also, during the manufacturing process of prefilled, ready-to-use syringes, the plunger brake 6 prevents, for example, the plunger 4 from being forced out of the barrel 1 due to excess pressure occurring in the interior during the post-sterilization of solutions previously filled into the barrel 1.

Figure 2:
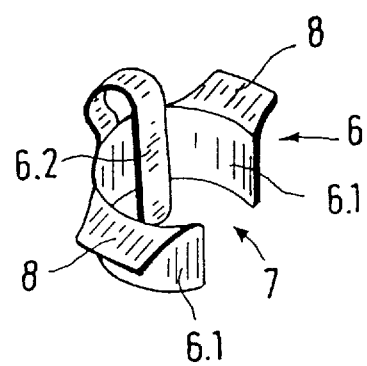

The annular portion 6.1 of the plunger brake 6, as shown in FIG. 2, consists of a separation slit 7 located on the side opposite the finger 6.2, as a result of which the plunger brake 6 can be clipped especially easily onto the syringe barrel 1 from the side. The annular portion 6.1 itself has an essentially sleeve-like shape, and is thus adapted in shape to the syringe barrel 1.

To improve handling, the annular piece 6.1 can be provided, in a way not shown in detail in the drawing, on its outer surface, with a riffling running in the circumferential direction. In addition, or alternatively, as shown in FIG. 2, the annular piece 6.1 can be provided with two radially extending, diametrically opposite wings 8, which form a finger rest. This is especially advantageous in the case of barrels with relatively small volume, since these generally do not have finger rests.

As FIG. 1 shows, the finger 6.2 lies against the inner wall of the syringe barrel 1, so that the piston rod 5 can be moved freely.

The piston rod 5 is tapered in the area 9 adjacent to the piston rod threads, so that the piston rod threads can be screwed into the plunger 4 without further efford, even when the plunger brake 6 is clipped into place.

Figure 3A:
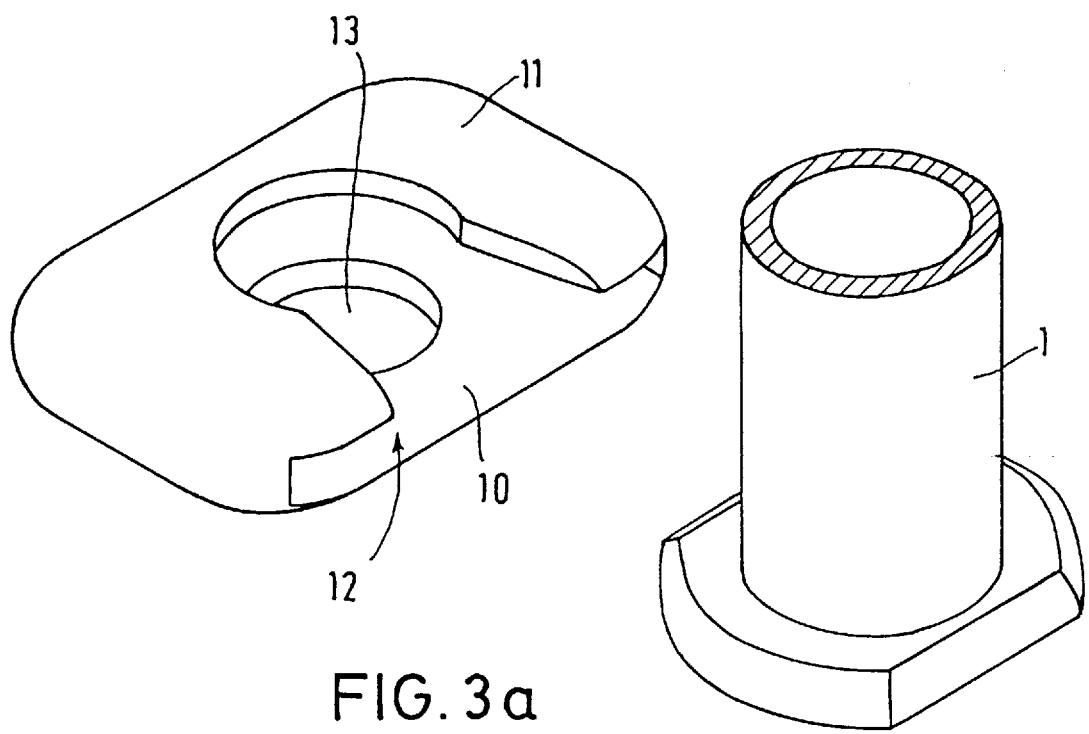
Figure 3B:
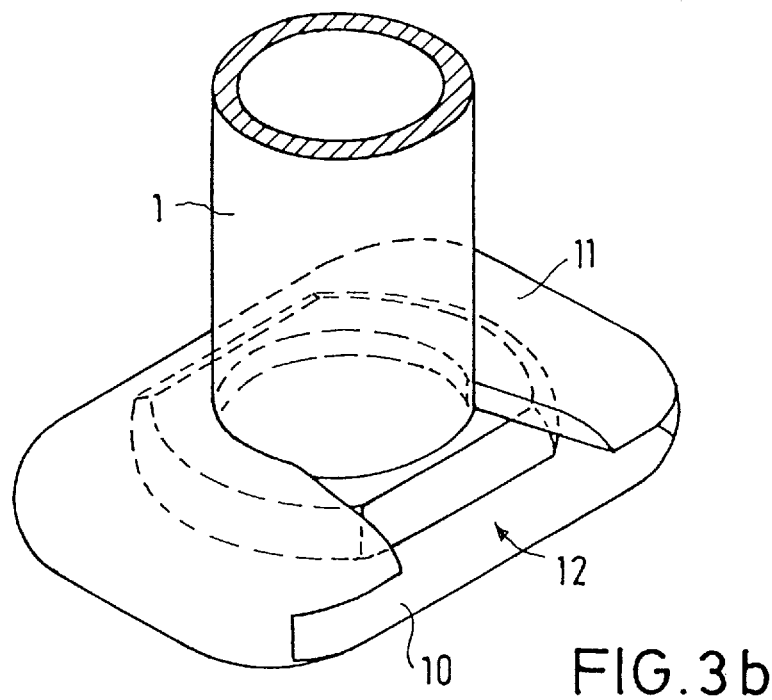

In the additional embodiment of the invention shown in FIGS. 3 and 4, the rest piece is formed by a flat slip-on piece made up of two disks 10,11 positioned at a distance from one another. The two disks 10,11 are connected at the edge, and between themselves form a receiving pocket 12, open toward one edge, for the radially outwardly extending edge of the syringe barrel 1.

The disk 10 away from the adapter 2 is provided with a circular opening 13 coaxial with the syringe barrel 1, the diameter of which opening is smaller than the internal diameter of the syringe barrel 1, so that the edge of this opening 13 forms the stop for the plunger 4. The other disk 11 has a recess 14, open toward the edge, for the syringe cylinder 1, so that this can be slid into the recess 14 from the side.

As is especially recognizable in FIG. 4, the recess 14 has an edge 5 that is coaxial to the opening 13 and is shaped like the arc of a circle, surrounding the syringe barrel 1 by somewhat more than 180 degrees. In this way, firm retention of the slip-on piece on the syringe cylinder 1 is guaranteed. The recess 14 also broadens in the direction of the edge of the disk 11, simplifying the attachment of the slide-on piece to the syringe barrel 1.

Figure 5:
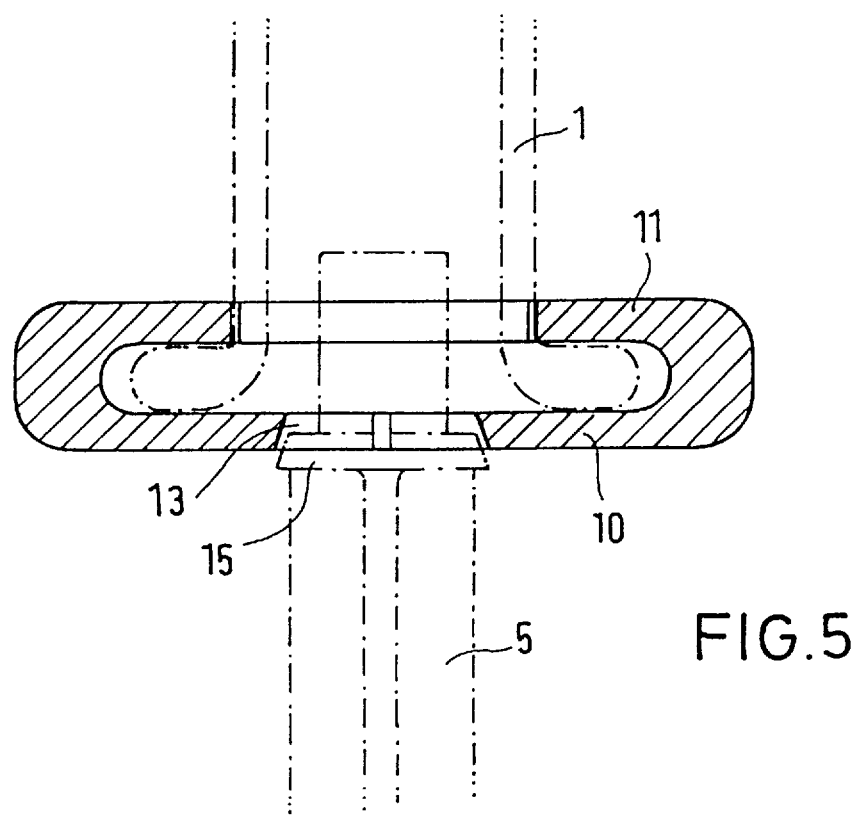
Figure 6:
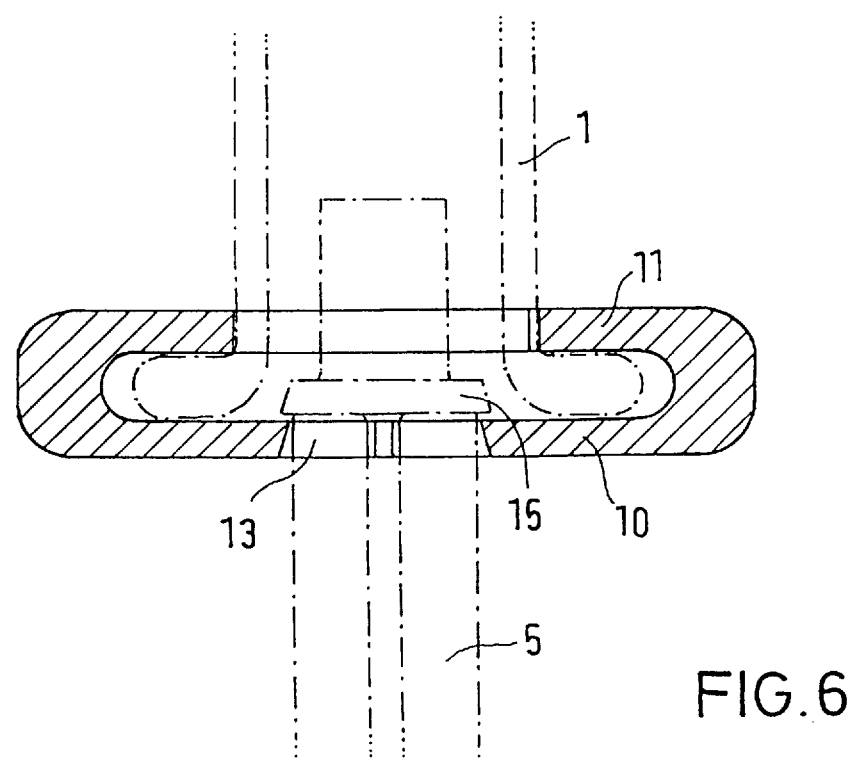

In addition, in order to prevent the piston rod from being able to be pulled out of the syringe barrel, the wall of the opening 13—as shown in FIGS. 5 and 6—is designed as a conical mantle surface tapering toward the adapter 2. The piston rod 5 has, at its end facing the plunger, a radially outwardly extending annular flange 15, the outer jacket surface of which likewise tapers conically, wherein the circular opening 13 and/or the annular flange 15 are designed to be elastic, at least in the edge area.

The dimensions are selected such that the annular flange 15 is received in a form-locking manner by the circular opening 13. In this way, to be sure, the piston rod can be slid into the syringe barrel 1, wherein the two conical surfaces of the circular opening 13 and the annular flange 15 slip past one another, but cannot be pulled out again, as is clearly apparent from FIG. 6.

We claim:

1. A syringe comprising an elongate hollow barrel having a distal end, an open proximal end and a chamber therebetween for retaining fluid, said barrel defining an inside diameter, a tip at said distal end of said barrel having a passageway therethrough in fluid communication with said chamber, a plunger rod assembly including a piston in slidable fluid tight engagement with the inside diameter of said barrel, an elongate plunger rod connected to said piston and extending proximally through said open end of said barrel and a complementary protrusion provided on the plunger assembly, a plunger rod assembly brake removably attached to said open proximal end of said barrel including a rest piece housing portion partially surrounding and removably engaging said open proximal end of said barrel, said rest piece housing portion including a projection wing for applying axial force to said barrel, said projection wing emanating radially from said rest piece housing portion, and said plunger rod assembly brake including a projection for engaging said complementary protrusion on said plunger rod assembly so that proximal movement of said plunger rod assembly with respect to said barrel will cause said projection and said complementary protrusion to engage and prevent removal of said plunger rod assembly from said barrel during normal use of said syringe.

2. The syringe of claim 1 wherein said brake projection includes at least one finger extending axially into said chamber, said at least one finger including a distal end having an end surface for contacting said complementary protrusion of said plunger rod assembly to prevent removal of said plunger rod assembly from said barrel.

3. The syringe of claim 2 wherein said finger is in contacting relationship with said barrel in said chamber.

4. The syringe of claim 1 wherein said rest piece housing portion includes a circularly shaped side wall having an inside surface for contacting said barrel.

5. The syringe of claim 4 wherein said circularly shaped side wall includes a discontinuity of less than 180°.

6. The syringe of claim 5 wherein said discontinuity is on the opposite side of said brake from said projection.

7. The syringe of claim 1 wherein said rest piece housing portion is sleeve shaped.

8. The syringe of claim 1 wherein said complementary protrusion includes an annular flange on said plunger rod radially extending from a longitudinal axis of said plunger rod.

9. The syringe of claim 8 wherein said annular flange has a tapered frusto-conically shaped outside diameter.

10. The syringe of claim 1 wherein said barrel includes a radially outwardly extending barrel projection at said open proximal end, and said plunger rod assembly brake includes a planar element proximally spaced from said rest piece housing portion and connected to said rest piece housing portion to form a pocket containing said radially outwardly extending barrel projection, said planar element including an opening therethrough, said brake projection being formed in said opening.

11. The syringe of claim 10 wherein said opening is circular and said brake projection is formed around said opening, said brake projection defining a diameter smaller than the inside diameter of said barrel.

12. The syringe of claim 11 wherein said brake projection defines a frusto-conically shaped mantle formed through the planar element and defining a first diameter on the proximal side of said planar element and a second diameter on said distal side of said planar element which is smaller than said first diameter.

13. The syringe of claim 12 wherein said complementary protrusion on said plunger rod includes an annular flange radially extending from a longitudinal axis of said plunger rod.

14. The syringe of claim 13 wherein said disk-shaped structure has a tapered frusto-conically shaped outside diameter being larger on the proximal side of said disk than on said distal side of said disk.

* * * * *